United States Patent
Dzwiniel et al.

(10) Patent No.: US 11,028,065 B1
(45) Date of Patent: Jun. 8, 2021

(54) CONTINUOUS METHOD FOR PREPARING CARBONATE ESTERS

(71) Applicant: UCHICAGO ARGONNE, LLC, Chicago, IL (US)

(72) Inventors: Trevor L. Dzwiniel, Carol Stream, IL (US); Krzysztof Pupek, Plainfield, IL (US)

(73) Assignee: UCHICAGO ARGONNE, LLC, Argonne, IL (US)

( * ) Notice: Subject to any disclaimer, the term of this patent is extended or adjusted under 35 U.S.C. 154(b) by 0 days.

(21) Appl. No.: 16/812,628

(22) Filed: Mar. 9, 2020

(51) Int. Cl.
*C07C 69/96* (2006.01)
*C07D 317/40* (2006.01)
*B01J 31/02* (2006.01)

(52) U.S. Cl.
CPC ........ *C07D 317/40* (2013.01); *B01J 31/0232* (2013.01); *C07C 69/96* (2013.01)

(58) Field of Classification Search
CPC ..... C07D 317/40; B01J 31/0232; C07C 69/96
USPC .......................................... 549/229; 558/260
See application file for complete search history.

(56) References Cited

U.S. PATENT DOCUMENTS

2017/0066710 A1    3/2017    Ma et al.

FOREIGN PATENT DOCUMENTS

CN    108101739 A    6/2018

OTHER PUBLICATIONS

Liu et al, Multifunctional Phosphonium-Based Deep Eutectic Ionic Liquids: Insights into Simultaneous Activation of CO2 and Epoxide and Their Subsequent Cycloaddition, ACS Sustainable Chem. Eng., 2019, 7, 16674-16681 (Year: 2019).*
Wikipedia, Acetonitrile, Nov. 2018, p. 1-7). (Year: 2018).*
Miao et al, Catalytic Processes for Chemical Conversion of Carbon Dioxide into Cyclic Carbonates and Polycarbonates The Open Organic Chemistry Journal, 2008, 2, 68-82. (Year: 2008).*
Dzwiniel, T. et al., Synthesis of New Electrolyte Solvents via Continuous Flow Manufacturing, SelectBIO Conference, Coronado Island, CA,, 1-10 (2019).
Dzwiniel, T. et al., Continuous Flow Chemistry: Advanced Manufacturing for Electrolyte Materials, Flow Chemistry & Continuous Processing, Boston, MA., 1-11 (2019).

* cited by examiner

*Primary Examiner* — Taylor V Oh
(74) *Attorney, Agent, or Firm* — Olson & Cepuritis, Ltd.

(57) ABSTRACT

In one embodiment, a continuous process for preparing organic carbonate solvent of Formula (I) as described herein comprises contacting a first reactant (an alcohol) with a reactive carbonyl source (carbonyldiimidazole (CDI) or an alkylchloroformate) in the presence of a catalyst in reaction stream flowing through a continuous flow reactor at temperature 20° C. to about 160° C. and at a flow rate providing a residence time in the range of about 0.1 minute to about 24 hours; collecting a reactor effluent exiting from the continuous flow reactor; recovering a crude product from the reactor effluent; and distilling the crude product to obtain the organic carbonate compound of Formula (I). In another embodiment, the first reactant is an epoxide and the carbonyl source is carbon dioxide.

14 Claims, 4 Drawing Sheets

CONTINUOUS METHOD FOR PREPARING CARBONATE ESTERS

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

This invention relates to a continuous method for preparing carbonate esters, which are useful, e.g., in non-aqueous solvents and electrolytes for electrochemical cells and batteries.

BACKGROUND

Organic carbonate ester compounds have been found to be useful as electrolyte solvents for non-aqueous electrochemical cells and batteries (e.g., lithium batteries). Numerous carbonate esters have been utilized in rechargeable battery systems, including linear carbonates and cyclic carbonates. In some cases, conventional batch processes to prepare the carbonate esters can be expensive and difficult to scale up.

There is an ongoing need for new methods of preparing organic carbonate esters for use, e.g., in rechargeable battery systems. The methods described herein address this ongoing need.

SUMMARY OF THE INVENTION

A continuous processes for preparing organic carbonate solvent of Formula (I) is described herein.

(I)

In Formula (I) Z is a covalent bond; x is 0 or 1; $R^1$ is $C_1$-$C_6$ alkyl or $C_1$-$C_6$ fluoroalkyl bearing at least one fluoro substituent; $R^2$ is H, $C_1$-$C_6$ alkyl or $C_1$-$C_6$ fluoroalkyl bearing at least one fluoro substituent. When x is 0, both $R^3$ and $R^4$ are $CH_2$ and are not directly bonded together. When x is 1, $R^3$ and $R^4$ both are CH, $R^2$ is H, and $R^3$ and $R^4$ are directly connected by a covalent bond.

The process described herein involves contacting an alcohol or an epoxide with a reactive carbonyl source (e.g., an alkyl chloroformate, a fluoroalkyl chloroformate, carbonyldiimidazole (CDI), or carbon dioxide) in the presence of a catalyst in a continuous flow reactor at a temperature in the range of about 20° C. to about 160° C. Typically, the alcohol or epoxide is dissolved in an aprotic solvent e.g., at a concentration of about 0.5 to 6 M, and the catalyst and carbonyl source are dissolved in the same solvent. Typical residence times for the processes described herein are about 0.1 minute to about 24 hours, depending on the internal volume of the reactor, the temperature, solvent, catalyst, the other reactants, and the like. In practice, the reaction stream is pumped through the heated reactor at temperature, flow rate, and residence time sufficient to achieve a desired level of conversion of the alcohol or epoxide to the compound of Formula (I), e.g., complete or maximal conversion. Optionally, any remaining carbonyl source is quenched before recovering a crude product from a reactor effluent flowing out of the reactor. The crude product is then purified, e.g., by distillation to obtain the organic carbonate compound of Formula (I). Scheme 1 illustrates three embodiments (A, B, and C) of the process.

Scheme 1.

Scheme 1, A, illustrates a process wherein an alcohol of Formula (II) is reacted with an alkyl chloroformate or fluoroalkyl chloroformate as the carbonyl source, wherein R and R' are independently $C_1$-$C_6$ alkyl or $C_1$-$C_6$ fluoroalkyl bearing at least one fluoro substituent. Scheme 1, B, illustrates a process wherein the alcohol of Formula (II) is reacted with carbonyldiimidazole (CDI) as the carbonyl source (i.e., X(CO)X in which X is N-imidazolyl). Scheme 1, C, illustrates a process wherein an epoxide of Formula (III) is reacted with carbon dioxide as the carbonyl source.

Formula (Ia) in Scheme 1 corresponds to the organic carbonate of Formula (I) wherein x is 0 (i.e., a linear carbonate ester); $R^2$ and $R^3$ both are $CH_2$; R of Formula (Ia) corresponds to R of Formula (I); and R' of Formula (Ia) corresponds to $R^2$ of Formula (I).

Formula (Ib) in Scheme 1 corresponds to the organic carbonate of Formula (I) wherein x is 0; $R^3$ and $R^4$ both are $CH_2$; and the two R groups of Formula (Ib) correspond to $R^1$ and $R^2$ of Formula (I).

Formula (Ic) in Scheme 1 corresponds to the organic carbonate of Formula (I) wherein x is 1 (i.e., a cyclic carbonate ester), R³ and R⁴ both are CH; R² is H; and R of Formula (Ic) corresponds to R¹ of Formula (I).

The solvents utilized in the processes shown in Scheme 1 are aprotic solvents, preferably polar aprotic solvents, such as, for example, nitriles (e.g., acetonitrile), ethylene glycol ethers (e.g., glyme, diglyme, butyl methyl diethylene glycol ether, butyl methyl triethylene glycol ether), ketones (e.g., acetone or methylisopropylketone (MIK)), amides (e.g., dimethylformamide (DMF) or N-methylpyrrolidone (NMP)), organic carbonates (e.g., dimethyl carbonate (DMC) or diethyl carbonate (DEC)), phosphoramides (e.g., hexamethylphosphoramide (HMPA), other substituted phosphoramides, etc.), and the like.

The catalysts utilized in the processes shown in Scheme 1 comprise, for example, organic nitrogen-containing bases, organic phosphorus-compounds, and the like, such as, e.g., tertiary amines (e.g., diisopropylethylamine (DIPEA)); bicyclic amidines (e.g., 1,8-diazabicyclo[5.4.0]undec-7-ene (DBU)); phosphazenes (e.g., 2-tert-butylimino-2-diethyl-amino-1,3-dimethylperhydro-1,3,2-diazaphosphorine (BEMP)); bicyclic guanidines (e.g., 1,5,7-triazabicyclo[4.4.0]dec-5-ene (TBD)); quaternary ammonium salts (e.g., tetraalkylammonium halides, N-alkylated heterocycle salts, such as N-alkylpyridinium halides); quaternary phosphonium salts (e.g., methyltriphenylphosphonium bromide); acid addition salts of organic nitrogen-containing bases (e.g., hydrochloride salts, hydrobromide salts, hydroiodide salts, or organic acid salts of tertiary amines, amidines, guanidines, phosphazenes, nitrogen-heterocycles, and the like); and ionic liquids comprising ions of such catalysts.

The following non-limiting embodiments of the methods described herein are provided below to illustrate certain aspects and features of the present invention.

Embodiment 1 is a continuous processes for preparing organic carbonate solvent of Formula (I):

(I)

comprising the steps of:
(a) contacting a first reactant with a reactive carbonyl source in reaction stream containing a catalyst flowing through a continuous flow reactor at a temperature in the range of about 20° C. to about 160° C., and at a flow rate providing a residence time in the range of about 0.1 minute to about 24 hours;
(b) optionally quenching any remaining reactive carbonyl source;
(c) collecting a reactor effluent exiting from the continuous flow reactor;
(d) recovering a crude product from the reactor effluent; and
(e) purifying the crude product to obtain the organic carbonate compound of Formula (I);
wherein:
the reactive carbonyl source is selected from the group consisting of a chloroformate of formula $Cl(CO)OCH_2R'$, carbonyldiimidazole (CDI), and carbon dioxide;

when the carbonyl source is the chloroformate or CDI the first reactant is an alcohol of Formula (II):

(II)

when the carbonyl source is carbon dioxide the first reactant is an epoxide of Formula (III):

(III)

the catalyst comprises at least one material selected from the group consisting of a tertiary amine, a bicyclic amidine, a phosphazene, a bicyclic guanidine, a quaternary ammonium salt, a quaternary phosphonium salt, an acid addition salt of a tertiary amine, an acid addition salt of a bicyclic amidine, an acid addition salt of a phosphazene, an acid addition salt of a bicyclic guanidine; an acid addition salt of a nitrogen-heterocycle, and an ionic liquid comprising an ion of one or more of the foregoing catalysts;
Z is a covalent bond;
x is 0 or 1;
R is $C_1$-$C_6$ alkyl or $C_1$-$C_6$ fluoroalkyl bearing at least one fluoro substituent;
R² is H, $C_1$-$C_6$ alkyl or $C_1$-$C_6$ fluoroalkyl bearing at least one fluoro substituent;
when x is 0, both R³ and R⁴ are $CH_2$ and are not directly bonded together;
when x is 1, R³ and R⁴ both are CH, R¹ is H, and R³ and R⁴ are directly connected by a covalent bond; and
R and R' independently are $C_1$-$C_6$ alkyl or $C_1$-$C_6$ fluoroalkyl comprising at least one fluoro substituent.

Embodiment 2 is the process of embodiment 1, wherein the reaction stream further comprises an aprotic organic solvent in which the first reactant, the carbonyl source, and the catalyst are dissolved; and preferably the alcohol or epoxide is dissolved in the solvent at a concentration of about 0.5 to about 6 molar (M).

Embodiment 3 is the process of embodiment 1 or 2, wherein the aprotic organic solvent comprises at least one material selected from the group consisting of an ether, a nitrile, an ester, an organic carbonate ester, an amide, a ketone, a sulfone, a sulfoxide, a hydrocarbon, a halogenated hydrocarbon, a phosphoramide, and an ionic liquid.

Embodiment 4 is the process of any one of embodiments 1 to 3, wherein each of R¹ and R² independently is $C_1$ to $C_4$ alkyl or C to $C_4$ fluoroalkyl.

Embodiment 5 is the process of any one of embodiments 1 to 4, wherein the compound of Formula (I) is purified in step (e) by distillation.

Embodiment 6 is the process of any one of embodiments 1 to 5, wherein the first reactant is the alcohol of Formula (II), the carbonyl source is the chloroformate of formula $Cl(CO)OCH_2R'$; the catalyst is selected from the group consisting of a tertiary amine, an aromatic nitrogen heterocycle, and a quaternary ammonium hydroxide; the catalyst is present in the reaction stream at a concentration of about 100 to 150 mol % relative to the alcohol; and the reaction stream comprises an aprotic organic solvent selected from the group consisting of a nitrile, a glycol ether, and ketone in which the alcohol, the chloroformate and the catalyst are dissolved.

Embodiment 7 is the process of embodiment 6, wherein the alcohol is dissolved in the solvent at a concentration of about 0.5 to about 6 molar (M).

Embodiment 8 is the process of embodiment 6, wherein the solvent comprises acetonitrile.

Embodiment 9 is the process of embodiment 6, wherein the catalyst comprises diisopropylethylamine.

Embodiment 10 is the process of embodiment 9, wherein the alcohol is 2,2,2-trifluoroethanol; the carbonyl source is methylchloroformate; the catalyst is diisopropylethylamine; the solvent is acetonitrile; the alcohol is dissolved in the solvent at a concentration of about 0.5 to 6 M; and the continuous flow reactor is heated at a temperature in the range of about 30° C. to about 110° C.

Embodiment 11 is the process of any one of embodiments 1 to 5, wherein the first reactant is the alcohol of Formula (II); the carbonyl source is the CDI; the catalyst is selected from the group consisting tertiary amine, an aromatic nitrogen heterocycle, and a quaternary ammonium hydroxide; the catalyst is present in the reaction stream at a concentration of about 2 to 15 mol % relative to the alcohol; and the reaction stream comprises an aprotic organic solvent selected from the group consisting of a nitrile, an ester, an organic carbonate ester, an amide, a ketone, a sulfone, a sulfoxide, a halogenated hydrocarbon, a phosphoramide, and an ionic liquid, in which the alcohol, the CDI, and the catalyst are dissolved; and preferably the alcohol is dissolved in the solvent at a concentration of about 0.5 to about 6 molar (M).

Embodiment 12 is the process of embodiment 11, wherein the alcohol is 2,2,2-trifluoroethanol.

Embodiment 13 is the process of embodiment 11, wherein the solvent comprises dimethylformamide.

Embodiment 14 is the process of embodiment 11, wherein the alcohol is present in the reaction stream in a respective molar ratio of alcohol-to-CDI of about 1.8:1 to about 2.6:1.

Embodiment 15 is the process of embodiment 11, wherein the alcohol is 2,2,2-trifluoroethanol; the solvent is selected from the group consisting of dimethylformamide, acetonitrile, acetone, and dimethylsulfoxide; the alcohol is present in the reaction stream in a respective molar ratio of alcohol to CDI of about 2:1 to about 3:1; and the continuous flow reactor is heated at a temperature in the range of about 50 to about 120° C.

Embodiment 16 is the process of any one of embodiments 1 to 5, wherein the first reactant is the epoxide of Formula (III); the carbonyl source is carbon dioxide; the catalyst is selected from the group consisting of an acid addition salt of a bicyclic amidine, an acid addition salt of a phosphazene, an acid addition salt of a bicyclic guanidine, a quaternary ammonium halide, and a quaternary phosphonium halide; the catalyst is present in the reaction stream at a concentration of about 1 to 20 mol % relative to the epoxide; the carbon dioxide is present in the reaction stream at a pressure in the range of about 1 to about 10 bar; and the reaction stream comprises an aprotic organic solvent selected from the group consisting of a nitrile, an ester, an organic carbonate ester, an amide, a ketone, a sulfone, a sulfoxide, and a halogenated hydrocarbon; and preferably, the epoxide is dissolved in the solvent at a concentration of about 0.5 to about 6 molar (M).

Embodiment 17 is the process of embodiment 16, wherein the reaction stream flowing through the continuous flow reactor is heated at a temperature in the range of about 50° C. to about 120° C.

Embodiment 18 is the process of embodiment 16, wherein the solvent comprises acetonitrile.

Embodiment 19 is the process of embodiment 16, wherein the epoxide comprises 3,3,3,-trifluoropropylene-1,2-oxide.

Embodiment 20 is the process of embodiment 19, wherein the solvent is acetonitrile; the catalyst is selected from the group consisting of tetrabutylammonium bromide, tetrabutylammonium chloride, tetrabutylammonium iodide, and benzyltriethylammonium bromide; the catalyst is present at a concentration of about 1 to about 15 mol % relative to the epoxide; and the continuous flow reactor is heated at a temperature in the range of about 50° C. to about 120° C.

DETAILED DESCRIPTION

In one aspect, a continuous process for preparing a linear organic carbonate solvent of Formula (I) (i.e., wherein x is 0) is described. The process comprises contacting an oxygen-containing reactant (i.e., an alcohol in this aspect) with a reactive carbonyl source (carbonyldiimidazole (CDI) or a chloroformate) in the presence of a catalyst in reaction stream flowing through a continuous flow reactor at a temperature of about 20° C. to about 160° C. Typically the reaction stream is pumped through the reactor at a flow rate providing a residence time of about 1 minute to about 24 hours. A reactor effluent containing the product compound of Formula (I) is collected as the effluent exits the continuous flow reactor. The crude product is recovered from the reactor effluent (e.g., by evaporation of solvent, precipitation extraction or any other expedient method. Purified carbonate ester of Formula (I), wherein x is 0, is obtained by distilling the crude product. In another aspect, the oxygen-containing reactant is an epoxide, the carbonyl source is carbon dioxide, and the product is a compound of Formula (I) wherein x is 1 (i.e., a cyclic carbonate).

In one embodiment (see Scheme 1, A), a continuous process for preparing an organic carbonate of Formula (Ia) is provided, wherein R is $C_1$-$C_6$ alkyl (e.g., methyl, ethyl, propyl, isopropyl) or $C_1$-$C_6$ fluoroalkyl comprising at least one fluoro substituent (e.g., $CF_3$, $FCH_2$, $CF_3CH_2$, $CF_3CH_2CH_2$, $CF_3CF_2$, $CF_3CF_2CF_2$, and the like); and R' is $C_1$-$C_6$ alkyl (e.g., methyl, ethyl, propyl, isopropyl, butyl) or $C_1$-$C_6$ fluoroalkyl comprising at least one fluoro substituent (e.g., $CF_3$, $FCH_2$, $CF_3CH_2$, $CF_3CH_2CH_2$, $CF_3CF_2$, $CF_3CF_2CF_2$, and the like). The method comprises contacting an alcohol of Formula (II) as described herein with a chloroformate compound (Cl—(CO)—OR', wherein R' is $C_1$-$C_6$ alkyl (e.g., methyl, ethyl, propyl, isopropyl) or $C_1$-$C_6$ fluoroalkyl comprising at least one fluoro substituent) in the presence of a catalyst in a reaction stream flowing through a continuous flow reactor heated at a temperature in the range of about 20° C. to about 160° C., at a flow rate providing a residence time of about 1 minute to about 24 hours; quenching any remaining chloroformate compound; collecting an effluent stream exiting from the continuous flow reactor; recovering a crude product from the so-collected effluent stream; and distilling the crude product to obtain the compound of Formula (Ia). The catalyst preferably comprises a tertiary amine such as trimethylamine, triethylamine, tributylamine, diisopropylethylamine, and the like. The catalyst typically is utilized at a concentration relative to the alcohol of about 100 to about 150 mol % (i.e., a molar percentage based on the molar concentration of the alcohol). In preferred embodiments the reaction stream comprises an aprotic organic solvent such as acetonitrile, acetone, dimethylformamide, dimethylsulfoxide, and the like. Typically, the alcohol and the chloroformate are dissolved in solvent in the reaction stream at concentrations ranging from about 0.5 to about 6 M. Optionally, the reaction can be performed neat (i.e., with no solvent).

In another embodiment (see Scheme 1, B), a continuous process for preparing a compound of Formula (Ib) is provided wherein R is $C_1$-$C_6$ alkyl (e.g., methyl, ethyl, propyl, isopropyl, butyl, pentyl, etc.) or $C_1$-$C_6$ fluoroalkyl comprising at least one fluoro substituent (e.g., $CF_3$, $FCH_2$, $CF_3CH_2$, $CF_3CH_2CH_2$, perfluoroethyl, perfluoropropyl, perfluorobutyl, perfluoropentyl, etc.). The method comprises contacting an alcohol of Formula (II) as described herein with carbonyldiimidazole (CDI) in the presence of a catalyst in a reaction stream flowing through a continuous flow reactor heated at a temperature of about 20° C. to about 160° C., and a flow rate providing a residence time of about 1 minute to about 24 hours; quenching any remaining CDI; collecting an effluent stream exiting from the continuous flow reactor; recovering a crude product from the so-collected effluent stream; and distilling the crude product to obtain the compound of Formula (Ib). The catalyst preferably comprises a tertiary amine, such as trimethylamine, triethylamine, tributylamine, diisopropylethylamine, and the like. The catalyst typically is utilized at a concentration relative to the alcohol of about 1 to about 10 mol %. In preferred embodiments the reaction stream comprises an aprotic organic solvent such as acetonitrile, acetone, dimethylformamide, dimethylsulfoxide, and the like. In some embodiments, at least about two equivalents of the alcohol are contacted with the CDI. Typically, the alcohol is dissolved in solvent in the reaction stream at a concentration of about 0.5 to about 6 M, and the concentration of the alcohol in the reaction stream is at least twice the concentration of the CDI. Optionally, the reaction can be performed neat (i.e., with no solvent).

In yet another embodiment (see Scheme 1, C), a continuous process for preparing a compound of Formula (Ic) is provided wherein R is $C_1$-$C_6$ alkyl (e.g., methyl, ethyl, propyl, isopropyl, butyl, pentyl, etc.) or $C_1$-$C_6$ fluoroalkyl comprising at least one fluoro substituent (e.g., $CF_3$, $FCH_2$, $CF_3CH_2$, $CF_3CH_2CH_2$, perfluoroethyl, perfluoropropyl, perfluorobutyl, perfluoropentyl, etc.). The method comprises contacting an epoxide of Formula (III) as described herein with carbon dioxide at a pressure in the range of about 1 to about 10 bar in in the presence of a catalyst in a reaction stream flowing through a continuous flow reactor heated at a temperature in the range of about 50° C. to about 120° C. and a flow rate providing a residence time in the range of about 1 minute to about 24 hours; collecting an effluent stream exiting from the continuous flow reactor; recovering a crude product from the so-collected effluent stream; and distilling the crude product to obtain the compound of Formula (Ic). The catalyst preferably comprises a quaternary ammonium halide salt, such as tetrabutylammonium bromide (TBAB), or an N-alkylated aromatic nitrogen heterocycle. The catalyst typically is utilized at a concentration relative to the epoxide of about 5 to about 20 mol %. In some embodiments the reaction stream comprises an aprotic organic solvent such as acetonitrile, acetone, dimethylformamide, and the like. Typically, the epoxide is dissolved in a solvent in the reaction stream at a concentration of about 0.5 to about 6 M. Optionally, the reaction can be performed neat (i.e., with no solvent).

In some embodiments, a continuous process for manufacturing a compound of Formula (I) wherein x is 0 involves simultaneously pumping a first solution comprising the alcohol of Formula (II) and the catalyst in a first aprotic solvent, and a second solution of the activated carbonyl compound (e.g., CDI, the chloroformate) in a second aprotic solvent (which can be the same or different from the first aprotic solvent) together in a continuous flow-reactor vessel heated at a temperature in the range of about 20° C. to about 160° C., where the first and second solutions mix together to form a reaction stream. The reaction stream flows through the heated reactor vessel, optionally with in-line active or static mixing, and an effluent comprising the compound of Formula (I) flows out of the vessel and is collected. Solvents are then removed from the effluent (e.g., by evaporation or washing with an aqueous solvent) and the resulting crude product of Formula (I) is isolated and purified, e.g., by distillation.

In another embodiment, a continuous process for manufacturing a compound of Formula (I) wherein x is 1 involves pumping a reaction stream comprising the epoxide of Formula (III) (either neat or dissolved in an aprotic solvent) and the catalyst through a continuous flow-reactor vessel heated at a temperature in the range of about 20° C. to about 160° C., and simultaneously introducing carbon dioxide into the reaction stream (e.g., at a pressure of about 1 to about 10 bar). The reaction stream flows through the heated reactor vessel, optionally with in-line active or static mixing, and an effluent comprising the compound of Formula (I) flows out of the vessel and is collected. Any solvent is removed from the effluent (e.g., by evaporation or washing with an aqueous solvent), and the resulting crude product of Formula (I) is isolated and purified (e.g., by distillation). In some embodiments, the carbon dioxide is introduced into the reaction stream by a mass flow controller and standard in-line mixer.

The heated continuous flow reactor vessel typically is either a glass micro-reactor or a tube (e.g., a coil of tubing)

within a heating chamber (e.g., a furnace or heating bath, or a tube that includes one of more heating elements (e.g., heating tape) in contact with the tube. Preferably, the reaction stream has a residence time of about 1 minute to about 24 hours within the heated reactor vessel. The vessel includes an opening (e.g., the other end of the tube from where the solution are being pumped) that allows the effluent stream to exit the heated vessel for collection. As the solution or solutions are continuously pumped into and through the vessel, the effluent containing the product continuously flows out of the vessel for collection.

Typical residence times for the processes described herein are in the range of about 0.1 minute to about 24 hours. Residence time (RT) is dependent on the flow rate (Q) and the volume of the reactor (V), i.e., RT=V/Q. The desired temperature, flow rate and residence time, are selected, at least in part, based on the reactor volume, the desired manufacturing throughput, and the desired level of conversion of alcohol or epoxide to the compound of Formula (I). Typically the concentrations, relative amounts, and the chemical reactivity of reagents (e.g., alcohol, epoxide, and carbonyl source, catalyst), as well as the choice of solvent will be taken into account when choosing operating parameters for the flow reactor, as is well known for other types of chemical reactions. For extremely long reactor coils/large volumes, the RT can be quite long, even though the flow rate or throughput is good. In addition, the internal volume of solvent present in the reactor prior to pumping through the reactants (the void volume) must be displaced by the reaction stream before product effluent is collected. This can take a long time before product-containing effluent is collected, but then collection can be achieved at a good rate.

The temperature and residence time within a heated portion of the reactor are selected so that the reaction is substantially complete or at a maximum conversion by the time the effluent flows out of the heated portion of the reactor. For a given combination of carbonyl source and alcohol or epoxide, the catalyst, solvent, reactor temperature, flow rate, and residence time can be determined by routine process development principals and screening experiments which are well known in the chemical process art. The completeness of the reaction (conversion) can be monitored by, e.g., by gas chromatography, liquid chromatography, or thin-layer chromatography to determine when the alcohol, epoxide, the carbonyl source, or any combination thereof, are no longer detected, or when production of the product compound of Formula (I) has reached a maximum. At least some byproducts of the reaction (e.g., imidazole) typically are removed from the effluent by washing with a suitable solvent (e.g., an aqueous solvent), which also can remove some or most of the reaction solvent (e.g., if the reaction solvent is water-soluble or water-miscible). The resulting crude carbonate ester of Formula (I) can then be purified, e.g., by distillation.

Figure 1:
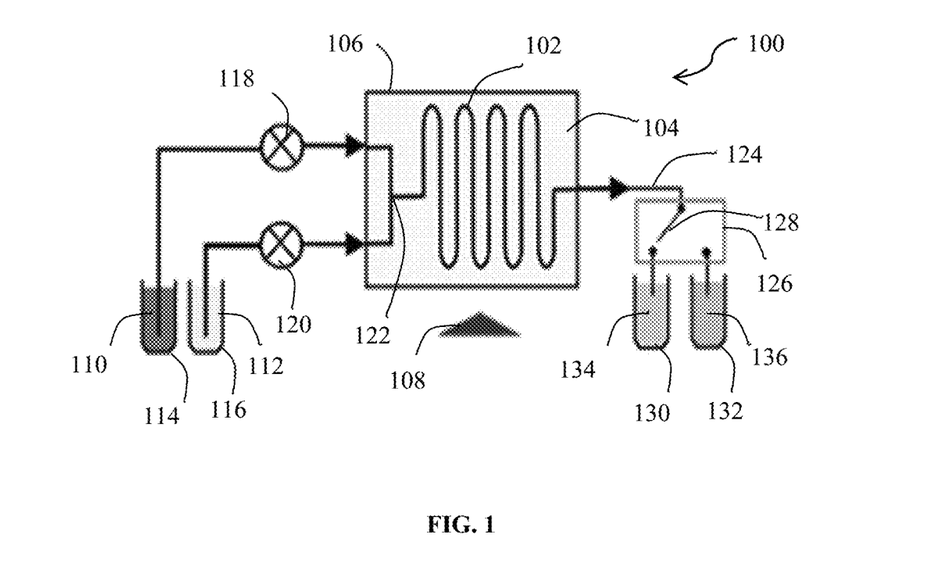
FIG. 1 schematically illustrates a continuous flow reactor system.

FIG. 1 schematically illustrates continuous flow reactor system 100, which comprises a coiled tubular reactor vessel housed within a heatable chamber 104 defined by a housing 106. Chamber 104 is heated by heating unit 108 operably connected with chamber 104. In use, a first solution 110 comprising a first reactant dissolved in a first solvent is pumped into reactor vessel 102 by pump 118 from first reservoir 114, while a second solution 112 comprising a second reactant dissolved in a second solvent is pumped into reactor vessel 102 by pump 120 from second reservoir 116, and the chamber 104 is heated at a desired temperature value by heating unit 108. First solution 110 and second solution 112 are mixed together at junction 122 as the solutions enter the reactor vessel 102. The combined solutions form a reaction stream that flows through vessel 102 and exits reactor vessel 102 through effluent line 124, and through valve 126 into either first collection vessel 130 or second collection vessel 132, depending on the position of a binary valve line 128 within valve 126. In practice, vessel 102 typically is prefilled with a solvent which is heated to the desired temperature, and the reaction stream displaces the prefilled solvent. In such cases, first collection vessel 130 is utilized to collect the prefill solvent effluent 134. Once the volume of prefill solvent has been displaced, valve 126 can be adjusted to direct effluent 136 comprising a reaction product into second collection vessel 132. The arrow heads in FIG. 1 indicate the direction of flow for the solutions, and effluent stream.

Non-limiting examples of suitable continuous flow reactors for use in the methods described herein include CORNING ADVANCED-FLOW reactors (also known as CORNING AFR reactors). According to the manufacturer, Corning Inc. (Corning, N.Y.), the CORNING AFR series of reactors are available in models that accommodate flow rates in the range of 2 to 10 mL/min (laboratory scale) up to 1000 to 8000 mL/min (the model G4 SiC reactor). Examples of such reactors are described, e.g., in International Patent Publication No. WO 2016/201211 to Gremetz et al., which is incorporated herein by reference in its entirety. Other examples of flow reactors include the flow reactors from Syrris Ltd., Royston, UK, such as the ASIA brand of reactors, and other lab scale reactors.

The catalysts utilized in the processes shown in Scheme 1 comprise, e.g., tertiary amines; bicyclic amidines, phosphazenes, bicyclic guanidines, quaternary ammonium salts (e.g., tetraalkylammonium halides such as tetrabutylammonium bromide, and N-alkylated heterocycle salts such as N-alkylpyridinium halides), quaternary phosphonium salts, acid addition salts of organic nitrogen-containing bases (e.g., hydrochloride salts, hydrobromide salts, hydroiodide salts, or organic acid salts of tertiary amines, amidines, guanidines, phosphazenes, nitrogen-heterocycles, and the like), and ionic liquids containing ions of such materials.

Non-limiting examples of tertiary amine catalysts include, e.g., diisopropylethylamine (DIPEA), triethylamine (TEA), tributylamine (TBA). Non-limiting examples of quaternary ammonium catalysts include, e.g., tetrabutylammonium halides (e.g., a chloride, bromide, or iodide salt), tetraethylammonium halides, N-alkylpyridinium halides, and N-alkyl-DBU halides. Non-limiting examples of quaternary phosphonium catalysts include, e.g., methyltriphenylphosphonium halides (e.g., a chloride, bromide, or iodide salt). Non-limiting examples of bicyclic amidine catalysts include, e.g., 1,8-diazabicyclo[5.4.0]undec-7-ene (DBU), 1,5-diazabicyclo[4.3.0]non-5-ene (DBN), 1,5-diazabicyclo [4.4.0]dec-5-ene (DBD), and the like. Non-limiting examples of bicyclic guanidine catalysts include, e.g., 1,5,7-triazabicyclo[4.4.0]dec-5-ene (TBD), 7-methyl-1,5,7-triazabicyclo-[4.4.0]dec-5-ene (MTBD), 7-ethyl-1,5,7-triazabicyclo-[4.4.0]dec-5-ene (ETBD), 7-isopropyl-1,5,7-triazabicyclo-[4.4.0]dec-5-ene (ITBD), and the like. Non-limiting examples of phosphazene catalysts include, e.g., 2-tert-butylimino-2-diethylamino-1,3-dimethylperhydro-1, 3,2-diazaphosphorine (BEMP), 1-tert-butyl-4,4,4-tris-(dimethylamino)-2,2-bis[tris(dimethylamino)-phosphoranylidenamino]-$2\lambda^5,4\lambda^5$-catenadi(phosphazene) ($P_4$-t-Bu), and the like. Non-limiting examples of acid addition salts of organic nitrogen-containing bases include, e.g., hydrochloride salts, hydrobromide salts, hydroiodide salts, and organic acid addition salts of tertiary amines, amidines, guanidines, phosphazenes, nitrogen-heterocycles, and the like, such as tributylamine hydrobromide, diisopropylethylamine hydrobromide, and DBU hydrobromide. In some embodiments, two or more of the catalysts can be used together.

Solvents that are useful in the methods described herein are aprotic organic solvents, such as ethers, nitriles, esters, organic carbonates, amides, ketones, sulfones, sulfoxides, phosphoramides, hydrocarbons, and halogenated hydrocarbons. In some embodiments, polar aprotic solvents are preferred (e.g., acetonitrile, N,N-dimethylformamide (DMF), sulfolane, dimethylsulfoxide, and the like).

Non-limiting examples of suitable ether solvents include diethyl ether, THF, 1,3-dioxolane, dioxane, and alkylene glycol ethers such as dimethoxyethane (DME or glyme), bis(2-methoxyethyl) ether (diglyme), diethylene glycol butyl methyl ether (MeO-DEG-OBu), and triethylene glycol butyl methyl ether (MeO-TEG-OBu). Non-limiting examples of suitable nitrile solvents include acetonitrile, propionitrile, butyronitrile, and the like. Non-limiting examples of suitable ester solvents include methyl acetate, ethyl acetate, propyl acetate, isobutyl acetate, ethyl butyrate, methyl propionate, and the like. Non-limiting examples of suitable organic carbonate solvents include ethylene carbonate (EC), propylene carbonate (PC), dimethyl carbonate, ethyl methyl carbonate, and the like. Non-limiting examples of suitable amide solvents include DMF, N,N-dimethylacetamide (DMAc), N-methylpyrrolidone (NMP), and the like. Non-limiting examples of suitable ketone solvents include acetone, methyl ethyl ketone (MEK), and the like. Non-limiting examples of suitable sulfone solvents include dimethylsulfone, sulfolane, and the like. A non-limiting example of a suitable sulfoxide solvents is dimethylsulfoxide. Non-limiting examples of suitable hydrocarbon solvents include aromatic hydrocarbons such as benzene, toluene, xylenes, and the like, as well as aliphatic hydrocarbons such as pentane, hexane, and the like. Non-limiting examples of suitable halogenated hydrocarbon solvents include aliphatic halogenated hydrocarbons such as dichloromethane (methylene chloride, trichloromethane (chloroform), hexachloroethane (perchloroethane), perfluoroalkanes, and the like; and aromatic halogenated hydrocarbons such as o-dichlorobenzene, m-dichlorobenzene, p-dichlorobenzene, 1,2,3-trichlorobenzene, 1,3,5-trichlorobenzene, 1,2,4-trichlorobenzene, hexachlorobenzene, 1-chloro-3-nitrobenzene, 1-bromo-4-chlorobenzene, and the like.

Ionic liquids, which are well known in the chemical arts, are commonly used as alternatives to organic solvents in many chemical reactions. In the present processes, ionic liquids comprising ions of the various catalysts described herein can be used as a solvent, a catalyst, or both. For example, ionic liquids comprising quaternary ammonium cations with a variety of different anions, e.g., tetraalkylammonium salts, and N-alkylated nitrogen-containing aromatic heterocyclic salts (e.g., N-alkylpyridinium salts, N,N-dialkylimidazolium salts, and the like) are well known in the ionic liquid art as solvents for organic synthesis (see, generally *Ionic Liquids in Synthesis*, Peter Wasserscheid and Tom Welton, Eds., WILEY-VHC Verlag GmbH & Co. KGaA, Weinheim, Germany (2007), which is incorporated herein by reference in its entirety; Chapter 2, pp. 7-55 thereof describes the synthesis of ionic liquids and various ionic liquid structures).

As used in reference to the methods described herein, the term "solution" refers to liquid compositions in which a material is dissolved in a solvent, as well as to liquid suspensions in which include a solid material suspended in a liquid vehicle. In such suspensions, the solid material may be partially or completely insoluble in the liquid vehicle such as an aprotic organic solvent or an ionic liquid.

As used herein, the term "alkyl" and grammatical variations thereof refers to a univalent saturated hydrocarbon group, i.e., saturated hydrocarbon lacking one hydrogen atom, e.g. methyl, ethyl, propyl, isopropyl, butyl, 1-methyl-1-propyl (also known as sec-butyl), 2-methyl-1-propyl (also known as isobutyl), pentyl, hexyl, cyclopenyl, cyclohexyl, and the like. Alkyl groups can include linear chains of carbons atoms (linear alkyl), branched chains of carbon atoms (branched alkyl), rings of carbon atoms (e.g., cycloalkyl), or any combination thereof. In some embodiments of the compounds of Formula (I), (II) and (III) an alkyl group can comprise 1 to 6 carbon atoms (also referred to as "$C_1$ to $C_6$ alkyl"), such as methyl, ethyl, propyl, and the like. In some embodiments, preferred alkyl groups include methyl and ethyl. Similarly, the term "fluoroalkyl" refers to an alkyl group, as described above, which includes at least one F substituent in place of a hydrogen thereof. The term "perfluoroalkyl" refers to an alkyl group, as described above, in which all of the hydrogens thereof are replaced by F.

As used herein the term "alkylene" refers to a bivalent saturated aliphatic radical (e.g., such as ethylene (—$CH_2CH_2$—), propylene (—$CH_2CH_2CH_2$—), and the like), which is formally regarded as derived from an alkene by opening of the double bond or from an alkane by removal of two hydrogen atoms from different carbon atoms. For example, an alkylene group can comprise 1 to 6 carbon atoms (also referred to as "$C_1$ to $C_6$ alkylene"), such as methylene (—$CH_2$—), ethylene (—$CH_2CH_2$—), linear propylene (e.g., —$CH_2CH_2CH_2$—), branched propylene (e.g., —$CH_2(CH_3)CH_2$—), and the like. As used herein, "alkylene glycol" refers to an ethylene or alkyl-substituted ethylene group bearing two hydroxyl substituents on the adjacent carbons of the ethylene moiety, as well as to oligomers of ethylene glycol and alkyl-substituted ethylene glycols, that have two terminal hydroxyl groups. The term "diethylene glycol" (DEG) refers to HO—$CH_2CH_2$—$CH_2CH_2$—OH, and "triethylene glycol" (TEG) refers to HO—$CH_2CH_2$—O—$CH_2CH_2$—O—$CH_2CH_2$—OH.

The following non-limiting Examples are provided to illustrate certain features of the compositions and methods described herein.

Example 1. Solvent and Catalyst Evaluation for Reaction of 2,2,2-trifluoroethanol with Methyl Chloroformate Batch reaction solubility experiments were performed with a series of solvents and bases for the reaction of 2,2,2-trifluoroethanol (72 μL) with methyl chloroformate (94 μL, 1.2 eq), using 1.1 mol equivalents of bases and 1.0 ml of solvent. Table 1 provides results for the solubility of the reaction mixture/product for the different catalyst (triethylamine (TEA), diisopropylethylamine (DIPEA), and Pyridine (Pyr)) and solvent (dichloromethane(DCM), dimethylformamide (DMF), dibutyl ethylene glycol ether (EG $(OBu)_2$), sulfolane, and acetonitrile (MeCN) combinations, where "insol" means a precipitate was observed; "sol" means no precipitate was observed, and "sol/2 phase" means there was no precipitate, but two phases were observed.

TABLE 1

|  | TEA | DIPEA | Pyr |
|---|---|---|---|
| DCM | insol | sol | sol |
| DMF | insol | sol | sol |

TABLE 1-continued

|  | TEA | DIPEA | Pyr |
|---|---|---|---|
| EG(OBu)$_2$ | insol | sol/2 phase | insol |
| Sulfolane | insol | sol/2 phase | sol |
| MeCN | insol | sol | sol |

Additional reaction solubility experiments were set up with a series of solvents and bases for the reaction of 2,2,2-trifluoroethanol (0.29 mL) with methyl chloroformate (0.37 mL, 1.1 eq), using 1.1 mol equivalents of base and 1.0 ml of solvent. Table 2 provides solubility screening results for the different catalyst (DIPEA, tributylamine (TBA), N-methylmorpholine (NMM), and imidazole (Imid)) and solvent (acetone, MeCN, butyl methyl diethylene glycol (MeO-DEG-OBu) and butyl methyl triethylene glycol (MeO-TEG-OBu)) combinations, where "insol" means a precipitate was observed; "sol" means no precipitate was observed. Reactions were worked up with the addition of water and the organic layer analyzed by GC coupled with mass spectrometry (GC/MS). GC/MS conversions for the same solvent/catalyst combinations are provided in Table 3.

TABLE 2

|  | DIPEA | Bu$_3$N (TBA) | NMM | Imid |
|---|---|---|---|---|
| Acetone | insol | sol | insol | sol |
| MeCN | sol | sol | insol | sol |
| MeO-DEG-OBu | insol | sol | insol | insol |
| MeO-TEG-OBu | insol | sol | insol | insol |

TABLE 3

|  | Acetone | MeCN | MeO-DEG-OBu | MeO-TEG-OBu |
|---|---|---|---|---|
| DIPEA | 83.3 | 94.3 | 91.9 | 92.9 |
| TBA | 86.0 | 89.3 | 74.89 | 79.4 |
| NMM | 80.0 | 70.7 | 75.4 | 87.3 |
| Imid | 78.0 | 61.1 | 83.3 | 83.2 |

From Tables 2 and 3, the preferred combination was determined to be acetonitrile and DIPEA (diisopropylethylamine).

Figure 2:
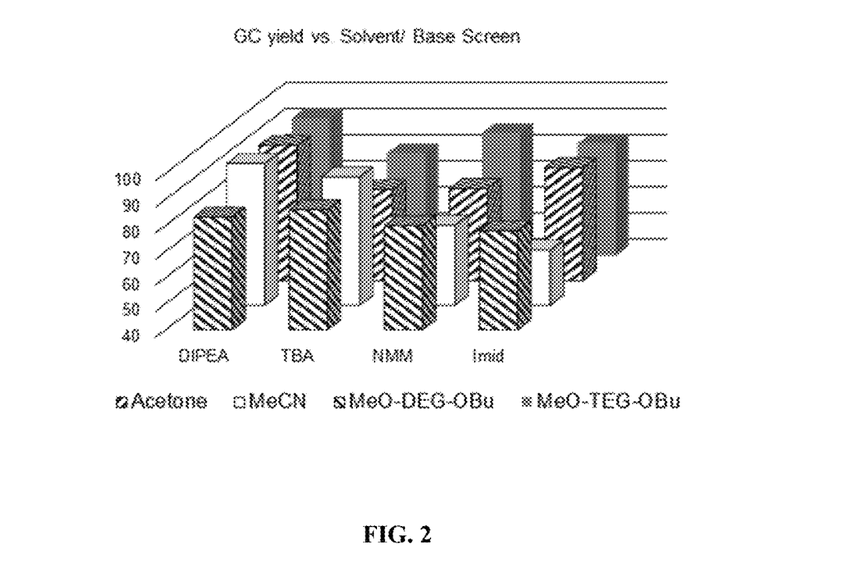
FIG. 2 provides graphs of reaction yield (as determined by gas chromatography (GC)) for the different solvent and base catalyst combinations for reaction of 2,2,2-trifluoroethanol with methyl chloroformate.

FIG. 2 provides graphs of reaction yield (as determined by GC) for the different solvent and base catalyst combinations for reaction of 2,2,2-trifluoroethanol with methyl chloroformate. The results shown in FIG. 2 indicate that a wide variety of solvents and catalysts can be utilized in this process.

Example 2. Solvent and Catalyst Evaluation for Continuous Flow Reaction of 2,2,2-trifluoroethanol with CDI Uncatalyzed TFE Formation—Comparison.

Solutions of 2,2,2-trifluoroethanol (TFE) in DMF (4 M concentration) and CDI (1 M) were prepared. These solutions were injected into a SYRRIS flow reactor system at a 2:1 molar ratio of alcohol to CDI at various reaction temperatures and residence times. The ratio of intermediate product in which only one imidazole is displaced by the TFE (TFE-O—C(O)—Imid) to desired product (bis-trifluoroethyl carbonate) was analyzed by GC/MS. Although formation of the desired product went up with temp and time, there was still a poor overall conversion (about 5 to 43%). Similar experiments were run with DMSO and with DMF using 2.1 and 2.2. equivalents of TFE relative to CDI, which did not show any significant improvement in conversion.

Catalyzed TFE Formation

Solutions of 2,2,2-trifluoroethanol (TFE) in DMF or acetonitrile (1 or 2 M containing 5 mol % DIPEA catalyst) and CDI (1 M in DMF or 0.5 M in acetonitrile) were prepared.

Reactions of TFE (1 M with 5 mol % DIPEA) and CDI (0.5 M) in acetonitrile; or TFE (2 M with 5 mol % DIPEA) and CDI (1 M) in DMF in a SYRRIS flow reactor system at a 2:1 molar ratio of alcohol to CDI at various reaction temperatures and a 2-minute residence time showed enhanced reactivity. The ratio of intermediate (TFE-O—C (O)—Imid) to desired product (F-DEC) was analyzed by GC/MS. All conditions gave substantially complete reaction as shown in Table 4. In Table 4, "Int." refers to the intermediate TFE-O—C(O)—Imid formed by displacement of one imidazole from CDI by TFE.

Reactions of TFE in DMF (2M with 5 mol % DIPEA) with pre-prepared TFE-O—C(O)—Imid (1 or 2 M) in DMF showed similarly enhanced reactivity with the catalyst present.

TABLE 4

|  | F-DEC* | Int. *. | Solution A | Solution B | % Conv | Mol Ratio TFE: CDI | Temp ° C. |
|---|---|---|---|---|---|---|---|
| 1 | 78.48 | 21.52 | 2M TFE/MeCN | 0.5M CDI | 78.48 | 1.8 | 100 |
| 2 | 81.21 | 18.79 | 2M TFE/MeCN | 0.5M CDI | 81.21 | 2.0 | 100 |
| 3 | 85.02 | 14.98 | 2M TFE/MeCN | 0.5M CDI | 85.02 | 2.2 | 100 |
| 4 | 87.16 | 12.84 | 2M TFE/MeCN | 0.5M CDI | 87.16 | 2.4 | 100 |
| 5 | 89.71 | 10.29 | 2M TFE/MeCN | 0.5M CDI | 89.71 | 2.6 | 100 |
| 6 | 78.84 | 21.17 | 2M TFE/MeCN | 0.5M CDI | 78.83 | 1.8 | 120 |
| 7 | 81.67 | 18.34 | 2M TFE/MeCN | 0.5M CDI | 81.66 | 2.0 | 120 |
| 8 | 85.48 | 14.52 | 2M TFE/MeCN | 0.5M CDI | 85.48 | 2.2 | 120 |
| 9 | 84.93 | 15.07 | 2M TFE/MeCN | 0.5M CDI | 84.93 | 2.4 | 120 |
| 10 | 89.02 | 10.98 | 2M TFE/MeCN | 0.5M CDI | 89.02 | 2.6 | 120 |
| 11 | 78.29 | 21.71 | 2M TFE/MeCN | 0.5M CDI | 78.29 | 1.8 | 140 |
| 12 | 84.99 | 15.01 | 2M TFE/MeCN | 0.5M CDI | 84.99 | 2.0 | 140 |
| 13 | 85.27 | 14.73 | 2M TFE/MeCN | 0.5M CDI | 85.27 | 2.2 | 140 |
| 14 | 87.61 | 12.39 | 2M TFE/MeCN | 0.5M CDI | 87.61 | 2.4 | 140 |
| 15 | 90.15 | 9.85 | 2M TFE/MeCN | 0.5M CDI | 90.15 | 2.6 | 140 |
| 16 | 84.12 | 15.88 | 2M TFE/MeCN | 0.5M CDI | 84.12 | 1.8 | 160 |
| 17 | 84.26 | 15.74 | 2M TFE/MeCN | 0.5M CDI | 84.26 | 2.0 | 160 |
| 18 | 86.41 | 13.59 | 2M TFE/MeCN | 0.5M CDI | 86.41 | 2.2 | 160 |
| 19 | 90.02 | 9.98 | 2M TFE/MeCN | 0.5M CDI | 90.02 | 2.4 | 160 |
| 20 | 90.98 | 9.01 | 2M TFE/MeCN | 0.5M CDI | 90.99 | 2.6 | 160 |

* = GC area under curve/10000

Figure 3:
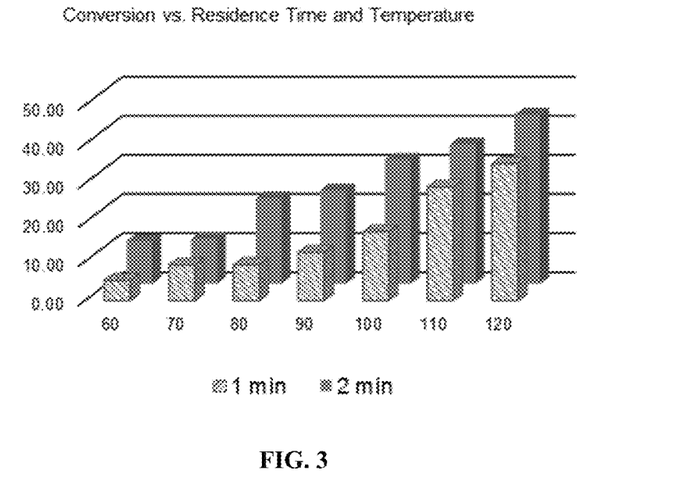
FIG. 3 provides a graph of conversion versus residence time and temperature for reaction of 2,2,2-trifluoroethanol with DCI.

FIG. 3 provides a graph of % conversion (vertical axis) versus residence time and temperature for reaction of 2,2,2-trifluoroethanol with DCI at temperatures from 60 to 120° C. (horizontal axis). The results shown in FIG. 3 indicate that conversion increases with both temperature and residence time.

Figure 4:
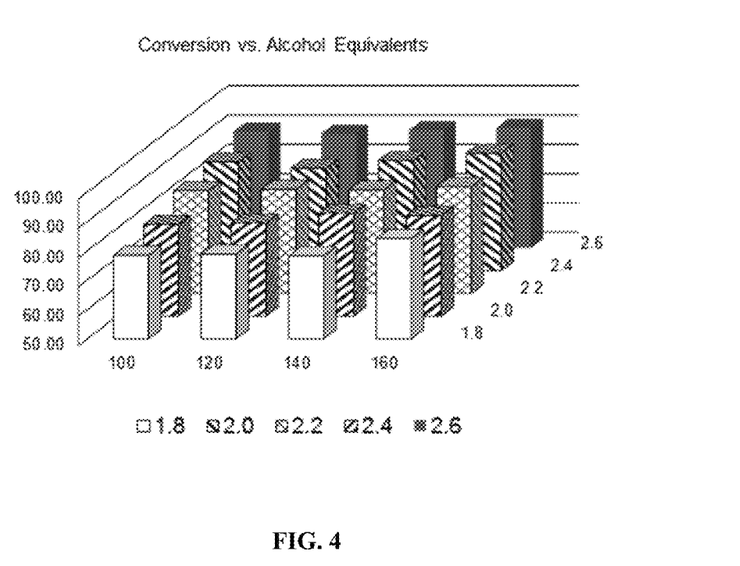
FIG. 4 provides a graph of conversion versus temperature and number of equivalents of 2,2,2-trifluoroethanol relative to CDI for reaction of 2,2,2-trifluoroethanol with DCI.

FIG. 4 provides a graph of % conversion (vertical axis) versus temperature (horizontal axis) and number of equivalents of 2,2,2-trifluoroethanol relative to CDI for reaction of 2,2,2-trifluoroethanol with DCI (from 1.8 to 2.6 equivalents) at 2-minute reaction time from the data in Table 4. The results in FIG. 4 and Table 4 indicate that conversion also increases with increasing number of equivalents of the alcohol, in addition to reaction temperature.

Example 3. Solvent and Catalyst Evaluation for Continuous Flow Reaction of 3,3,3-Trifluoropropylene Oxide with Carbon Dioxide General Batch Reaction Screening Procedure:

3,3,3-trifluoropropylene oxide (0.4 mL) and catalyst (10 mol %) were combined with acetonitrile or optionally another solvent (1 mL) in a test tube. The test tube was flushed with $CO_2$ gas either from a gas cylinder or from the addition of small chips of dry ice. The test tube was capped with a balloon and the reaction was stirred under about 1 atm of $CO_2$ for 24 hours. The mixture was then analyzed by gas chromatography couples with a mass spectrometry detector (GC/MS).

Alternate Batch Screening Procedure for Salt-Based Catalysts:

3,3,3-trifluoropropylene oxide (0.4 mL) and catalyst (10 mol %) were combined with acetonitrile (1 mL) in a 10 mL thick-walled reaction tube with a KONTES valve. The mixture was cooled in a −20° C. bath and dry $CO_2$ gas was purged into the tube for 30 seconds and sealed. The KONTES valve was closed and the reaction was stirred under this mild pressure of $CO_2$ for 24 hours at room temperature. The mixture was then analyzed by GC/MS.

Figure 5:
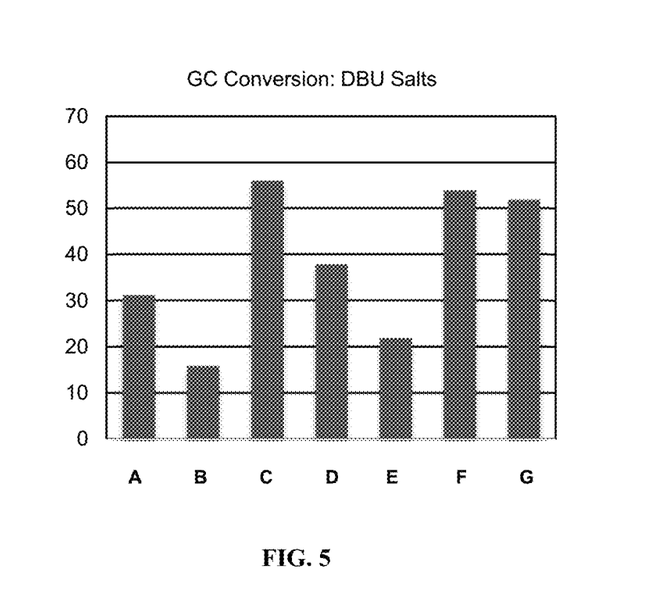
FIG. 5 provides a graph of conversion versus different DBU-based catalysts for reaction of 3,3,3-trifluoroproylene oxide with carbon dioxide in acetonitrile solvent.

Discussion of Screening Experiments:

FIG. 5 provides a graph of % conversion (vertical axis) versus different DBU-based catalysts (horizontal axis) for reaction of 3,3,3-trifluoroproylene oxide with carbon dioxide in acetonitrile solvent in the flow reactor experiments. The catalysts evaluated were A: DBU-acetic acid salt, B: DBU-lactic acid salt, C: DBU-hydrobromide salt, D: DBU-hydrochloride salt, E: DBU-propionic acid salt, F: 1N-(2-hydroxyethyl)-DBU bromide salt, and G: 1N-ethyl-DBU bromide salt.

Figure 6:
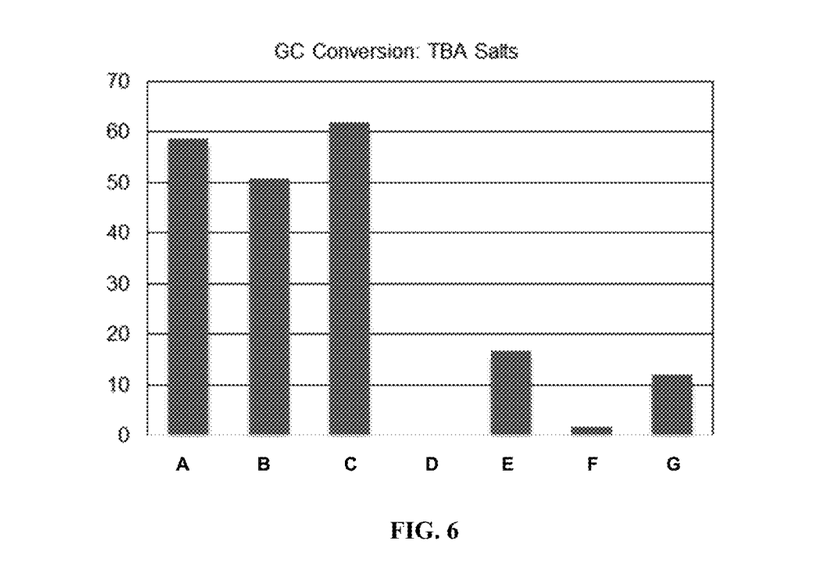
FIG. 6 provides a graph of conversion versus different tetrabutylammonium (TBA)-based catalysts for reaction of 3,3,3-trifluoropropylene oxide with carbon dioxide in acetonitrile solvent.

FIG. 6 provides a graph of % conversion (vertical axis) versus different tetrabutylammonium (TBA)-based catalysts (horizontal axis) for reaction of 3,3,3-trifluoroproylene oxide with carbon dioxide in acetonitrile solvent. The catalysts evaluated were A: tetrabutylammonium chloride, B: tetrabutylammonium iodide, C: tetrabutylammonium bromide, D: tetrabutylammonium hydrosulfate, E: tetrabutylammonium acetate, F: tetrabutylammonium fluoride, and G: tetrabutylammonium phosphate.

The results in FIG. 5 and FIG. 6 indicate that catalysts with chloride, bromide, and iodide anions outperformed all other anions. Mildly nucleophilic anions performed less well, and poorly nucleophilic anions either performed poorly or not at all.

Figure 7:
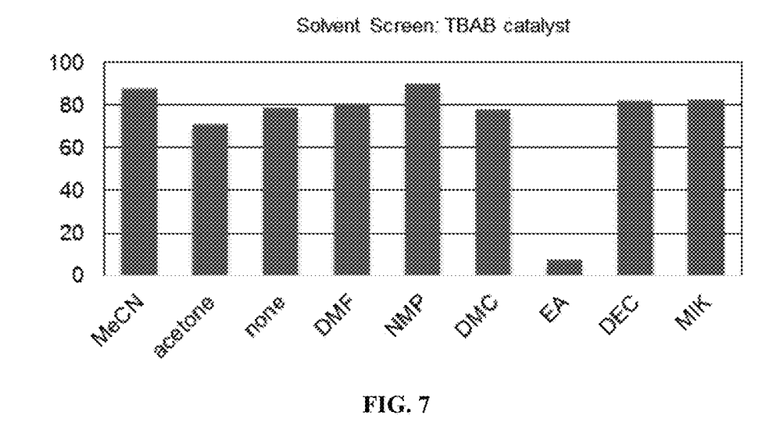
FIG. 7 provides a graph of conversion versus different solvents for reaction of 3,3,3-trifluoropropylene oxide with carbon dioxide in acetonitrile solvent with tetrabutylammonium bromide (TBAB) catalyst.

FIG. 7 provides a graph of % conversion versus different solvents (horizontal axis) for reaction of 3,3,3-trifluoroproylene oxide with carbon dioxide in acetonitrile solvent with tetrabutylammonium bromide (TBAB) catalyst. The results in FIG. 7 indicate that using TBAB, there is very little solvent effect with the exception of ethyl acetate (EA), which performed poorly.

Corning Flow Reactor Screening Tests:

3,3,3-Trifluoropropylene oxide (15 g) and catalyst (10 mol %) were combined with acetonitrile (45 mL) and pumped through a CORNING AFR reactor. The liquid flow rate was set to 5.00 mL/min, and the gas flow of $CO_2$ was set to 10.00 mL/min by a mass flow controller. The reaction temperature was set to 75° C. A back-pressure regulator was set to 2.5 bar. The outlet of the reactor was diverted back into the feedstock, allowing for the solution to flow through the reactor multiple times, so that a continuous loop was set up. Both due to reaction kinetics (slow) and ability to match the low mass flow rate of $CO_2$ to the higher rate of liquid flow, the solution was run through the reactor several times, simulating a longer, higher volume reactor tube. For the small reactor being used, the $CO_2$ would cause too many bubble/foaming on the outlet if the rate was set too high. Dropping the gas flow rate allowed smoother flow. This lower gas flow rate did, however, lead to lower conversion, which was the primary reason to recycle the solution. Finally, TBAB catalyst can discolor at higher temperatures, so it was desirable to keep the temperature relatively low. The solution was sampled for GC/MS analysis periodically. The results generally agree with small-scale testing, where catalysts with halide anions were most active. More effect of the cation was observed, showing that tetraalkylammonium was preferred, and tetrabutylammonium was most preferred.

Figure 8:
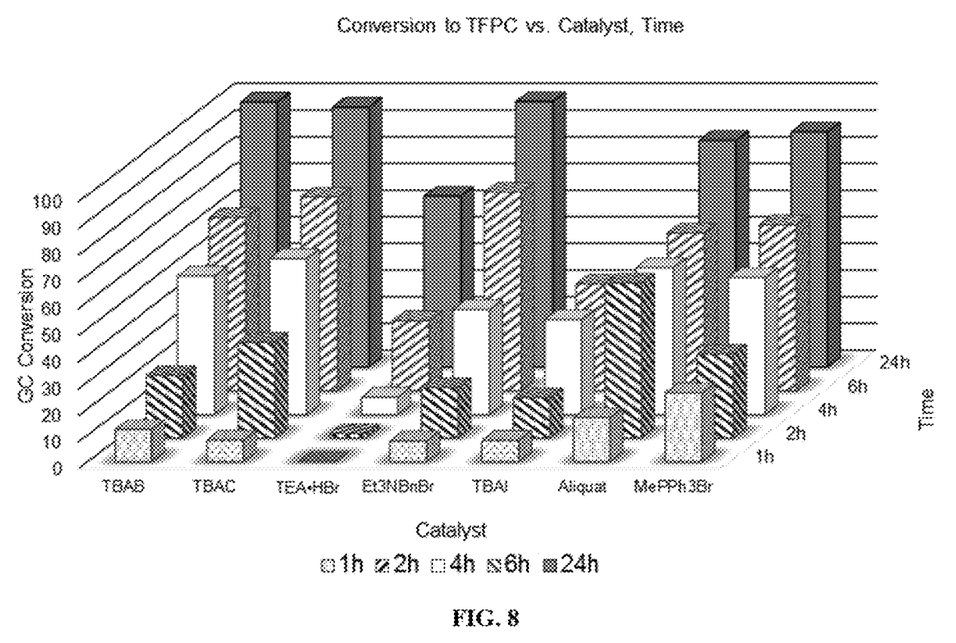
FIG. 8 provides graphs of conversion versus residence time for different catalysts for reaction of 3,3,3-trifluoropropylene oxide with carbon dioxide in acetonitrile solvent.

FIG. 8 provides graphs of % conversion versus residence time for different catalysts for reaction of 3,3,3-trifluoroproylene oxide with carbon dioxide in acetonitrile solvent in the flow reactor. The results in FIG. 8 indicate that the larger scale CORNING AFR flow reactor tests closely match the batch and small-scale flow reaction screening tests. The catalysts preferably have a halide anion and tetrabutylammonium cation.

Example 4. Continuous Flow Reaction Preparation of 2,2,2-Trifluoroethyl Methyl Carbonate (TFEMC)

A mixture of 2,2,2-trifluoroethanol (125.12 g) and DIPEA (177.76 g, 1.1 eq) was prepared. A solution of methyl chloroformate (142.87 g, "MCF", 3.25 eq) in acetonitrile (170.82 g) was prepared. The solutions were both pumped at 1.00 mL/min into the CORNING AFR reactor with a 2.7 mL volume flow reactor plate held at 50° C. Water was pumped at 1 mL/min into a second reaction plate attached to the outlet of the first plate to mix with the eluent of the first reactor plate and quench any remaining MCF. After several minutes, the flow rate of the MCF solution was lowered to 0.915 mL/min to minimize bubble formation out of the reactor system due to excess MCF. The entire collected eluent was titrated with 4N HCl to a yellow color. The layers were then separated. The product layer was washed with 10% HCl (2×20 mL), then brine (20 mL). The organic phase was then dried over anhydrous MgSO4. GC/MS showed 97.1% purity for the TFEMC product. The liquid was distilled through an Oldershaw distillation column to remove solvent and purify the TFEMC. Re-distillation of off-fractions provided 136 g of pure TFEMC (69% yield, GC/MS purity >99.9%).

Example 5. Continuous Flow Reaction Preparation of bis(2,2,2-trifluoroethyl) Carbonate (F-DEC)

A solution of 2,2,2-trifluoroethanol (50.19 g) and DIPEA (3.31 g, 0.05 equivalents) in acetonitrile (solution made to 300 mL total volume) was prepared. A second solution of CDI (39.71 g, 0.49 equivalents) in acetonitrile (solution made to 600 mL total volume) was prepared.

The first and second solutions were pumped into a 1 mL coil reactor held at 80° C. in a themostated oil bath at a rate of 1 mL/min and 2 mL/min, respectively. After about 50 mL of effluent had eluted, the remaining effluent was collected in a single main batch and analyzed. After collection, the liquid was distilled through an Oldershaw distillation column to remove acetonitrile, then to collect the pure product.

Example 6. Continuous Flow Reaction Preparation of Trifluoromethylpropylene Carbonate (TFPC)

A 500 mL 3-neck round bottom flask was charged with 3,3,3-trifluoropropylene oxide (100.86 g), TBAB catalyst (14.5970 g, 5 mol %), and acetonitrile (200 mL). The resulting mixture was magnetically stirred to dissolve the TBAB, and was then pumped through a CORNING AFR reactor at a rate of 5.5 mL/min, with a $CO_2$ gas flow rate of 23 mL/min (initial). The gas flow rate was adjusted as the reaction progressed to prevent large amounts of foaming and bubble formation from the outlet. The reaction temperature was set to 65° C. After one hour, the liquid flow rate was increased to 6.0 mL/min. The reactor output was put back into the round bottom flask, allowing the solution to circulate through the reactor system repeatedly. After 24 hours, an additional charge of TBAB (7.2050 g) was added to the flask and the reaction temperature was increased to 75° C. After 48 hours total reaction time, the reaction had progressed to 93% completion and elution was stopped. This eluent was combined with other small scale runs and distilled through a 5 plate Oldershaw column, first at 1 atm to remove acetonitrile and residual 3,3,3-trifluoropropylene oxide, then gradually reducing pressure to 0.6 Torr to distill the TFPC from the catalyst to provide 288 g (54% yield) of TFPC (GC purity >99.5%). Additional fractions were kept for further purification.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The terms "consisting of" and "consists of" are to be construed as closed terms, which limit any compositions or methods to the specified components or steps, respectively, that are listed in a given claim or portion of the specification. In addition, and because of its open nature, the term "comprising" broadly encompasses compositions and methods that "consist essentially of" or "consist of" specified components or steps, in addition to compositions and methods that include other components or steps beyond those listed in the given claim or portion of the specification. Recitation of ranges of values herein are merely intended to serve as a shorthand method of referring individually to each separate value falling within the range, unless otherwise indicated herein, and each separate value is incorporated into the specification as if it were individually recited herein. All numerical values obtained by measurement (e.g., weight, concentration, physical dimensions, removal rates, flow rates, and the like) are not to be construed as absolutely precise numbers, and should be considered to encompass values within the known limits of the measurement techniques commonly used in the art, regardless of whether or not the term "about" is explicitly stated. All methods described herein can be performed in any suitable order unless otherwise indicated herein or otherwise clearly contradicted by context. The use of any and all examples, or exemplary language (e.g., "such as") provided herein, is intended merely to better illuminate certain aspects of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The embodiments of the invention in which an exclusive property or privilege is claimed are defined as follows:

1. A continuous processes for preparing an organic carbonate solvent of Formula (I):

comprising the steps of:
(a) contacting a first reactant with a reactive carbonyl source in reaction stream containing a catalyst flowing through a continuous flow reactor at a temperature in the range of about 20° C. to about 160° C., and at a flow rate providing a residence time in the range of about 0.1 minute to about 24 hours;
(b) optionally quenching any remaining reactive carbonyl source;
(c) collecting a reactor effluent exiting from the continuous flow reactor;
(d) recovering a crude product from the reactor effluent; and
(e) purifying the crude product to obtain the organic carbonate compound of Formula (I);
wherein:
Z is a covalent bond;
x is 0;
R is $C_1$-$C_6$ alkyl or $C_1$-$C_6$ fluoroalkyl bearing at least one fluoro substituent;
$R^2$ is H, $C_1$-$C_6$ alkyl or $C_1$-$C_6$ fluoroalkyl bearing at least one fluoro substituent;
both $R^3$ and $R^4$ are $CH_2$ and are not directly bonded together;
R and R' independently are $C_1$-$C_6$ alkyl or $C_1$-$C_6$ fluoroalkyl comprising at least one fluoro substituent;
and wherein the first reactant is an alcohol of Formula (II):

the carbonyl source is a chloroformate of formula Cl(CO)OCH$_2$R'; the catalyst is selected from the group consisting of a tertiary amine, an aromatic nitrogen-containing heterocycle, and quaternary ammonium hydroxide, the catalyst is present in the reaction stream at a concentration of about 100 to 150 mol % relative to the alcohol; and the reaction stream comprises an aprotic organic solvent selected from the groups consisting of a nitrile, a glycol ether, and ketone in which the alcohol, the chloroformate, and the catalyst are dissolved.

2. The process of claim 1, wherein the alcohol is dissolved in the solvent at a concentration of about 0.5 to about 6 molar (M).

3. The process of claim 1, wherein the solvent comprises acetonitrile.

4. The process of claim 1, wherein the catalyst comprises diisopropylethylamine.

5. The process of claim 4, wherein the alcohol is 2,2,2-trifluoroethanol; the carbonyl source is methylchloroformate; the catalyst is diisopropylethylamine; the solvent is acetonitrile; the alcohol is dissolved in the solvent at a concentration of about 0.5 to 6 M; and the continuous flow reactor is heated at a temperature in the range of about 30° C. to about 110° C.

6. A continuous processes for preparing an organic carbonate solvent of Formula (I):

comprising the steps of:
(a) contacting a first reactant with a reactive carbonyl source in reaction stream containing a catalyst flowing through a continuous flow reactor at a temperature in the range of about 20° C. to about 160° C., and at a flow rate providing a residence time in the range of about 0.1 minute to about 24 hours;
(b) optionally quenching any remaining reactive carbonyl source;
(c) collecting a reactor effluent exiting from the continuous flow reactor;
(d) recovering a crude product from the reactor effluent; and
(e) purifying the crude product to obtain the organic carbonate compound of Formula (I);
wherein:
Z is a covalent bond;
x is 0;
$R^1$ is $C_1$-$C_6$ alkyl or $C_1$-$C_6$ fluoroalkyl bearing at least one fluoro substituent;
$R^2$ is H, $C_1$-$C_6$ alkyl or $C_1$-$C_6$ fluoroalkyl bearing at least one fluoro substituent;
both $R^3$ and $R^4$ are $CH_2$ and are not directly bonded together;
R is $C_1$-$C_6$ alkyl or $C_1$-$C_6$ fluoroalkyl comprising at least one fluoro substituent;

and wherein the first reactant is an alcohol of Formula (II):

the carbonyl source is carbonyldiimidazole (CDI); the catalyst is selected from the group consisting tertiary amine, an aromatic nitrogen-containing heterocycle, and a quaternary ammonium hydroxide; the catalyst is present in the reaction stream at a concentration of about 2 to 15 mol % relative to the alcohol; and the reaction stream comprises an aprotic organic solvent selected from the group consisting of a nitrile, an ester, an organic carbonate ester, an amide, a ketone, a sulfone, a sulfoxide, a halogenated hydrocarbon, a phosphoramide, and an ionic liquid, in which the alcohol, the CDI, and the catalyst are dissolved.

7. The process of claim 6, wherein the alcohol is 2,2,2-trifluoroethanol.

8. The process of claim 6, wherein the solvent comprises dimethylformamide.

9. The process of claim 6, wherein the alcohol is present in the reaction stream in a respective molar ratio of alcohol-to-CDI of about 1.8:1 to about 2.6:1.

10. The process of claim 6, wherein the alcohol is 2,2,2-trifluoroethanol; the solvent is selected from the group consisting of dimethylformamide, acetonitrile, acetone, and dimethylsulfoxide; the alcohol is present in the reaction stream in a respective molar ratio of alcohol to CDI of about 2:1 to about 3:1; and the continuous flow reactor is heated at a temperature in the range of about 50 to about 120° C.

11. The process of claim 1, wherein the first reactant is the epoxide of Formula (III); the carbonyl source is carbon dioxide; the catalyst is selected from the group consisting of an acid addition salt of a bicyclic amidine, an acid addition salt of a phosphazene, an acid addition salt of a bicyclic guanidine, a quaternary ammonium halide, and a quaternary phosphonium halide; the catalyst is present in the reaction stream at a concentration of about 1 to 20 mol % relative to the epoxide; the carbon dioxide is present in the reaction stream at a pressure in the range of about 1 to about 10 bar; and the reaction stream comprises an aprotic organic solvent selected from the group consisting of a nitrile, an ester, an organic carbonate ester, an amide, a ketone, a sulfone, a sulfoxide, and a halogenated hydrocarbon and wherein the epoxide is 3,3,3,-trifluoropropylene-1,2-oxide.

12. The process of claim 11, wherein the reaction stream flowing through the continuous flow reactor is heated at a temperature in the range of about 50° C. to about 120° C.

13. The process of claim 11, wherein the solvent comprises acetonitrile.

14. The process of claim 11, wherein the solvent is acetonitrile; the catalyst is selected from the group consisting of tetrabutylammonium bromide, tetrabutylammonium chloride, tetrabutylammonium iodide, and benzyltriethylammonium bromide; the catalyst is present at a concentration of about 1 to about 15 mol % relative to the epoxide; and the continuous flow reactor is heated at a temperature in the range of about 50° C. to about 120° C.

* * * * *

UNITED STATES PATENT AND TRADEMARK OFFICE
CERTIFICATE OF CORRECTION

PATENT NO. : 11,028,065 B1
APPLICATION NO. : 16/812628
DATED : June 8, 2021
INVENTOR(S) : Dzwiniel et al.

Page 1 of 1

It is certified that error appears in the above-identified patent and that said Letters Patent is hereby corrected as shown below:

In the Claims

Claim 1, Column 18, Line 43, delete "R" and insert --R'--.

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*